(12) United States Patent
Colli et al.

(10) Patent No.: US 10,538,479 B2
(45) Date of Patent: Jan. 21, 2020

(54) PROCESS FOR THE PREPARATION OF INDANAMINE DERIVATIVES AND NEW SYNTHESIS INTERMEDIATES

(71) Applicant: OLON S.P.A., Rodano (IT)

(72) Inventors: Corrado Colli, Rodano (IT); Alessandro Agosti, Rodano (IT); Stefano Maiorana, Milan (IT); Federica Colombo, Mariano Comense (IT); Giorgio Bertolini, Rodano (IT)

(73) Assignee: OLON S.P.A., Rodano (IT)

( * ) Notice: Subject to any disclaimer, the term of this patent is extended or adjusted under 35 U.S.C. 154(b) by 0 days.

(21) Appl. No.: 15/759,859

(22) PCT Filed: Sep. 28, 2016

(86) PCT No.: PCT/IB2016/001383
§ 371 (c)(1),
(2) Date: Mar. 14, 2018

(87) PCT Pub. No.: WO2017/055905
PCT Pub. Date: Apr. 6, 2017

(65) Prior Publication Data
US 2018/0258028 A1    Sep. 13, 2018

(30) Foreign Application Priority Data
Sep. 28, 2015   (IT) .............. UB2015A3978

(51) Int. Cl.
C07C 209/68 (2006.01)
C07C 211/42 (2006.01)
C07D 215/26 (2006.01)

(52) U.S. Cl.
CPC .......... C07C 209/68 (2013.01); C07C 211/42 (2013.01); C07D 215/26 (2013.01); C07C 2602/08 (2017.05)

(58) Field of Classification Search
None
See application file for complete search history.

(56) References Cited

U.S. PATENT DOCUMENTS

2007/0082897 A1*  4/2007  Strobel ............... C07C 233/58
                                                    514/227.8

FOREIGN PATENT DOCUMENTS

WO    0075114      12/2000
WO    03076387     9/2003

OTHER PUBLICATIONS

International Search Report and Written Opinion dated Dec. 20, 2016 for PCT/IB2016/001383.
Goksu S et al "Concise Syntheses of 2-aminoindans via indan-2-ol", Tetrahedron, Elsevier Science Publishers, Amsterdam, NL, vol. 61, No. 28, Jul. 11, 2005.
Francois Baur et al "The Identification of Indacaterol as an Ultralong-Acting Inhaled beta 2-Adrenoceptor Agonist", Journal of Medicinal Chemistry, vol. 53, No. 9, May 13, 2010.
Italian Search Report and Written Opinion of priority application No. IT UB20153978.
Mahavir Prashad et al. "Adv. Synth. Catal. 2001, 343, 461-472" Aug. 28, 2001—abstract.
International Preliminary Report on patentability dated Apr. 3, 2018 for PCT/IB2016/001383.
Office Action dated Mar. 27, 2019 for corresponding European patent application No. 16788192.9 and relevant reply filed with the EPO.

* cited by examiner

*Primary Examiner* — Sudhakar Katakam
*Assistant Examiner* — Jennifer C Sawyer
(74) *Attorney, Agent, or Firm* — Silvia Salvadori

(57) ABSTRACT

Subject-matter of the invention is a process for the preparation of key intermediates in the synthesis of indacaterol. Subject-matter of the invention are also new synthesis intermediates.

15 Claims, No Drawings

PROCESS FOR THE PREPARATION OF INDANAMINE DERIVATIVES AND NEW SYNTHESIS INTERMEDIATES

RELATED APPLICATIONS

This application is the US national phase application of international application number PCT/IB2016/001383, filed 28 Sep. 2016, which designates the US and claims priority to Italian application UB2015A003978 filed 28 Sep. 2015, the contents of each of which are hereby incorporated by reference as if set forth in their entireties.

A subject-matter of the invention is a process for the preparation of key intermediates in the synthesis of indacaterol. Another subject-matter of the invention are new synthesis intermediates.

TECHNICAL FIELD

Indacaterol is the international nonproprietary name of the compound (R)-5-[2-[(5,6-diethyl-2,3-dihydro-1H-inden-2-yl)amino]-1-hydroxyethyl]-8-hydroxyquinolin-2(1H)-one, having the following formula:

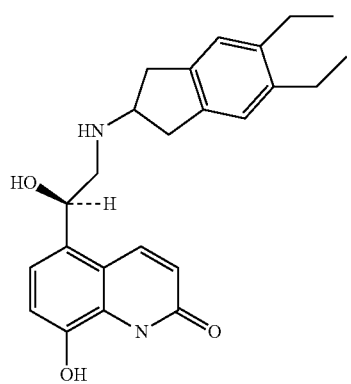 [SMILES: CCc1cc2c(cc1CC)CC(NC[C@@H](O)c1ccc(O)c3[nH]c(=O)ccc13)C2]

Indacaterol is a drug acting as selective agonist of beta-2 receptors and is recommended in the bronchospasm and in other bronchial pathological conditions such as bronchial asthma and the chronic obstructive pulmonary disease.

Some known synthesis of indacaterol make use of 4,5-diethyl-1H-inden-2-yl-amine as an intermediate having the following formula

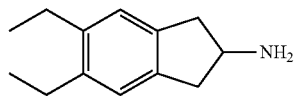

or N-substituted derivatives thereof, in particular the N-benzyl derivative, as key intermediates. Said intermediates are usually produced starting from the indanamine upon protection of the amine group. For example, WO03/076387 describes the preparation of 4,5-diethyl-1H-inden-2-yl-amine starting from the indanamine protected with trifluoroacetyl, by means of two consecutive Friedel-Crafts reactions, each followed by reduction of the introduced ketone group. The above indicated process has the drawback of requiring the isolation and purification of the obtained compounds after each individual reaction step, resulting in a process complexity related to the several isolations of the intermediates and, obviously, in a yield loss. Moreover, such process requires the wide use of chlorinated solvents, which must be then properly disposed thus affecting industrial costs.

WO00/75114 describes the preparation of 4,5-diethyl-1H-inden-2-yl-amine starting from diethylbenzene; the process results in very low yields and, in addition, the starting compound (diethylbenzene) is particularly expensive. These drawbacks make the process described in WO00/75114 of no industrial interest.

The document Adv. Synth. Catal. 2001, 343, 461-472 describes the preparation of 4,5-dibromo-1H-inden-2-yl-amine by direct bromination of 1H-inden-2-yl-amine with $Br_2$ and HBr. The Applicant reproduced the process described in such document and observed that the reported yield does not actually correspond to the pure compound but to a mixture of bromide compounds (mainly a monobromide derivative), which have then to be purified. Ultimately, by reproducing the process reported in the above cited document, a precipitate with the indicated weight is actually obtained but the yield of the desired product, after purification, is only about 25%. It is clear therefore that the process described in such document is not selective to form the dibromo at ortho, i.e. the 4,5-dibromo-1H-inden-2-yl-amine, since different variously brominated compounds are obtained which must undergo a purification, thus providing a very low yield, as mentioned.

There is therefore the need of finding a synthesis of the 4,5-dibromo-1H-inden-2-yl-amine and of 4,5-diethyl-1H-inden-2-yl-amine, which is of simple realization and does not require complex isolation and purification steps of the intermediates.

OBJECTS OF THE INVENTION

It is an object of the present invention to provide a process for the preparation of 4,5-dibromo-1H-inden-2-yl-amine which provides excellent yields and purity, while not requiring the purification from the synthesis by-products.

It is another object of the invention to provide a novel and convenient synthesis for the preparation of 4,5-diethyl-1H-inden-2-yl-amine or an N-derivative thereof.

It is another object of the invention to provide new synthesis intermediates in the preparation of indacaterol.

DESCRIPTION OF THE INVENTION

It has been now found that it is possible to prepare 4,5-dibromo-1H-inden-2-yl-amine by means of a simple synthesis, starting from 1H-inden-2-yl-amine with a bromination process which, contrary to what is described in the literature, provides the compound with excellent yield and purity.

Therefore object of the invention, according to one of the aspects thereof, is a process for the preparation of a compound of formula (I)

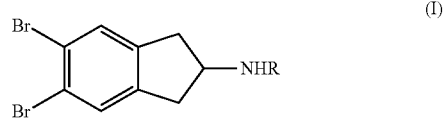

or the salts thereof, wherein R is a hydrogen atom or an amine protecting or activating group, comprising reacting the 1H-inden-2-yl-amine of formula (II)

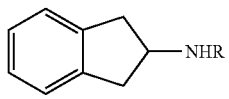

(II)

or a salt thereof, wherein R is as defined above with N-bromosuccinimide (NBS) in water, and optionally desalifying the so-obtained bromide compound and/or converting it into another salt and/or into a derivative thereof protected on the amine. Advantageously, the starting compound (II) is salified, preferably the hydrobromide or hydrochloride salt, the latter being preferred.

According to a preferred embodiment, R is hydrogen.

The "protecting or activating group of the amine" is a protecting group selected from the groups suitable to protect the amine, which group is however not brominated during the reaction, e.g. the acetyl or trifluoroacetyl group.

The molar ratio between the compound of formula (II) and NBS is about 1:2, preferably the NBS is used in slight excess with respect to twice the moles of the compound of formula (II), e.g. a preferred molar ratio is 1:1.8-2.5, advantageously 1:2.2.

According to a preferred embodiment, the reaction occurs in presence of an acid, advantageously a strong acid, such as for example concentrated sulfuric acid. Since the reaction occurs in water, the concentration of the used acid is not critical.

It has been observed that the presence of the acid catalyzes the reaction and allows greater conversion of the product of formula (II) into the desired compound, the reaction proceeds more quickly and goes to completeness. However, it is possible to carry out the reaction also without any acid, in any case the desired product is obtained.

The acid as well is used in slight excess with respect to the compound of formula (II), e.g. a preferred ratio compound (II):acid molar is about 1:2.

The reaction is carried out in water. The Applicant could noticed that the use of other solvents or the course of the reaction without any solvent does not lead to equivalent results, as it will be discussed below when commenting the examples and the comparative examples reported in the experimental section of the present description. The use of water is clearly an advantage in terms of costs and environmental impact. Moreover, the use of water allows to directly obtain the pure compound of formula (I), since it is the only reaction product which precipitates while the few by-products remain into the solution. This is a further advantage of the invention. The compound of formula (I) can be isolated by filtration from the reaction mixture with yields greater than 70% and with purity greater than 98%, even 99% (as measured by chromatographic methods such as UPLC or HPLC).

The reaction is preferably carried out at a temperature between the room temperature and the reflux temperature of the reaction mixture, advantageously at a temperature between 40 and 80° C., preferably at about 60° C. However, it has been observed that the temperature is not critical for the reaction which proceeds without the generation of by-products also by adding, from the beginning, a molar amount of NSB at least twice than the compound of formula (II) and always provides the desired product, as it will better highlighted from the examples reported below.

The reaction is completed within few hours and the expert in the field can follow its evolution by using well-known techniques, e.g. chromatography. As mentioned, the use of an acid facilitates the course of the reaction.

The compound of formula (I) is isolated from the reaction mixture by filtration, under the form of its hydrobromide salt and, if necessary or desired, it can be converted into the base or another salt according to known techniques.

Subject-matter of the invention, according to another of the aspects thereof, is the use of the compound of formula (I), or salts thereof, for the preparation of indacaterol. According to a preferred embodiment, for the preparation of indacaterol the compound of formula (I) undergoes a simultaneous double alkylation reaction to obtain the 3,5-diethyl-1H-inden-2-yl-amine of formula (III)

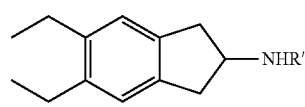

(III)

or the salts thereof, wherein R' is an amine protecting or activating group and includes acetyl, trifluoroacetyl, benzyl and substituted benzyl; the unsubstituted benzyl is a preferred protecting group.

The alkylation reaction can be realized by carrying out for example a Suzuki or Kumada coupling.

According to a preferred embodiment, the compound of formula (I) undergoes a Suzuki coupling reaction by initially attaching two vinyl groups and then reducing the double bonds to provide the desired compound. Alternatively, it is possible to perform a Kumada coupling, both with vinyl groups and following reduction, and to directly attach the two ethyl groups.

The coupling reactions referred above are known in the art, even though a double Kumada coupling is not common. Moreover, the Applicant observed that it is possible to carry out a Kumada coupling starting from the Grignard reagent on the aliphatic molecule instead of on the aromatic molecule, as it is usually performed. Detailed examples of these coupling reactions are provided in the experimental section of the present description.

According to another of the aspects thereof, subject-matter of the invention is a compound of formula (IV)

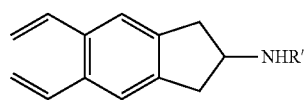

(IV)

or a salt thereof, wherein R' is as defined above, as well as its use as synthesis intermediate in the preparation of indacaterol.

When the preparation of the compounds of formula (III) and/or (IV) is desired, wherein the R and R' protecting groups are different, e.g. when an R'=benzyl group is used, it is possible to remove the R group and replace it with the R' group before or after the alkylation reaction.

Subject-matter of the invention, according to another of the aspects thereof, is a process for the preparation of the compound of formula (III), comprising reacting a compound of formula (II) as defined above with NBS in water, advantageously in the presence of an acid and then converting the so-obtained compound of formula (I) into a compound of formula (III).

According to a preferred embodiment, the reactions are carried out under the favorable and preferred conditions specified above.

EXPERIMENTAL SECTION

Example 1

Preparation of 4,5-dibromo-1H-inden-2-yl-amine (Compound of Formula (I) wherein R is Hydrogen) by Means of Two Bromination Steps

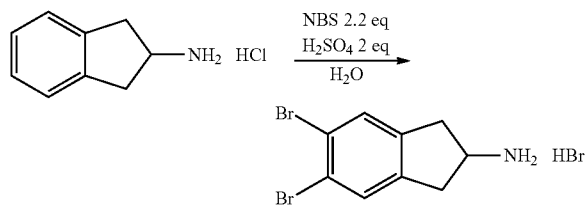

In a two neck flask equipped with a reflux, 5.26 g (31 mmol, 1 eq) of indanamine hydrochloride and 45 ml of $H_2O$ are charged. It is stirred at room temperature for 10 minutes and 5.52 g (31 mmol, 1 eq) of NBS and 3.52 ml (62 mmol, 2 eq) of conc. $H_2SO_4$ are added. It is left under stirring at room temperature for 1 hour and other 6.62 g (37.2 mmol, 1.2 eq) of NBS are added and it is heated up to 60° C. for 2 hours. It is cooled down to room temperature and filtered over buchner by washing the solid with 40 ml of $H_2O$. It is suspended in 16 ml of EtOH and left under stirring for 15 minutes and filtered over buchner. 8.49 g of the desired product are obtained (yield=73% purity 98-99%). The reaction is monitored by UPLC/MS.

In this case, the monobromide derivate formed initially (at room temperature), then the second equivalent of NBS is added and is heated up to push the second bromination occurring in ortho position with respect to the first.

Example 2

Preparation of 4,5-dibromo-1H-inden-2-yl-amine (Compound of Formula (I) Wherein R is Hydrogen) with a Single Bromination Step In a single neck flask equipped with a reflux, 500 mg (2.95 mmol, 1 eq) of indanamine hydrochloride and 5 ml of $H_2O$ are charged. It is stirred at room temperature for 10 minutes. 1.155 g (6.49 mmol, 2.2 eq) of NBS and 335 µl (5.9 mmol, 2 eq) of conc. $H_2SO_4$ are added. It is left under stirring at room temperature for 1 hour and then heated up to 60° C. for 1.5 hours. It is cooled down to room temperature and filtered over buchner by washing the solid with 4 ml of $H_2O$ and 770 mg of the desired product (yield=70% purity 98-99%) are obtained.

This test demonstrated that NBS is not necessarily charged at the beginning for stoichiometry of a bromine and then the remaining for the second bromination. However, the thermal profile of the starting standard test has been maintained, wherein the first bromination occurs under mild conditions, at room temperature, whereas the second occurs by heating to 60° C.

Example 3

Preparation of 4,5-dibromo-1H-inden-2-yl-amine (Compound of Formula (I) Wherein R is Hydrogen) with a Single Bromination Step In a single neck flask equipped with a reflux, 500 mg (2.95 mmol, 1 eq) of indanamine hydrochloride and 5 ml of $H_2O$ are charged. It is stirred at room temperature for 10 minutes. 1.155 g (6.49 mmol, 2.2 eq) of NBS and 335 µl (5.9 mmol, 2 eq) of conc. $H_2SO_4$ are added. It is then heated up to 60° C. for 3.5 hours. It is cooled down to room temperature and filtered over buchner by washing the solid with 4 ml of $H_2O$. 775 mg of the desired product are obtained (yield=71% purity 98-99%).

This test demonstrated that the temperature is not critical for the invention, since the two bromine atoms are immediately attached in the desired positions.

Example 4

Preparation of 4,5-divinyl-1H-inden-2-yl-amine by Suzuki Reaction

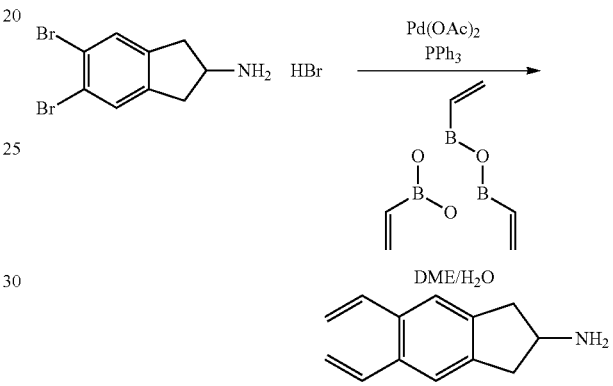

In a flask equipped with a reflux, 200 mg of dibromo indanamine hydrobromide, 12 mg of Pd(OAc)2, 35 ml of PPh3, 193 mg of 2,4,6-trivinyl-cyclo triboroxane pyridine complex and about 300 mg of $K_2CO_3$ are charged. 9 ml of dimethoxyethane and 2.6 ml of water are added. It is heated up to 90° C. for 2 hours. It is cooled down to room temperature and 10 ml of toluene and 5 ml of 2M HCl are added. The phases are separated and the aqueous phase is basified with NaOH. It is extracted with DCM and 90 mg of product are obtained (yield=90%).

By reducing the title compound, e.g. by catalytic hydrogenation, the 4,5-diethyl indanamine is prepared.

Example 5

Preparation of 4,5-divinyl-1H-inden-2-yl-amine by Kumada Reaction

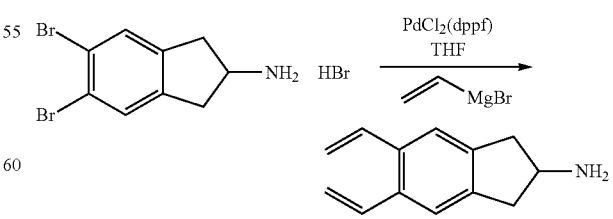

100 mg of the product are suspended in 2 ml of THF at room temperature and PdCl2 (0.05 eq.) is added. The Grignard compound (10 eq.) is added dropwise for 5 minutes and it is heated up at reflux for 4.5 hours. 45 mg of the product are obtained. By reducing the title compound, e.g. by catalytic hydrogenation, the 4,5-diethyl indanamine is prepared.

Example 6

Preparation of 4,5-diethyl-1H-inden-2-yl-amine by Kumada Reaction

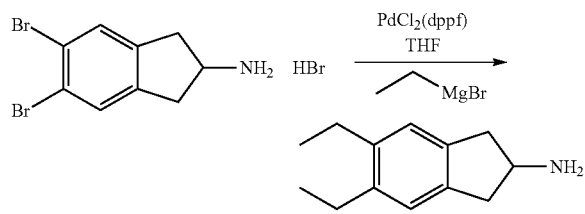

100 mg of dibromo indanamine hydrobromide are suspended in 2 ml of THF and PdCl2 (0.05 eq.) is added. The Grignard reagent (10 eq.) is added dropwise and it is heated up at reflux for 4 hours. About 46 mg of diethyl indanamine are obtained.

Comparative Example A

Preparation of 4,5-dibromo-1H-inden-2-yl-amine (Compound of Formula (I) Wherein R is Hydrogen) without Solvent In a single neck flask equipped with a reflux, 500 mg (2.95 mmol, 1 eq) of indanamine hydrochloride are charged. 1.155 g (6.49 mmol, 2.2 eq) of NBS and 335 µl (5.9 mmol, 2 eq) of conc. $H_2SO_4$ are added. It is then heated up to 60° C. for 5 hours and a solubility problem occurs, since a non-stirrable paste is obtained.

An UPLC/MS control already after 1 hour showed that 18% of monobromo product, 69% of dibromo compound, 9.5% of product with 3 bromines and 3% of product with 4 bromines, were produced.

Comparative Example B

Preparation of 4,5-dibromo-1H-inden-2-yl-amine (Compound of Formula (I) Wherein R is Hydrogen) in Acetonitrile In a single neck flask equipped with a reflux, 500 mg (2.95 mmol, 1 eq) of indanamine hydrochloride and 5 ml of $CH_3CN$ are charged. It is stirred at room temperature for 10 minutes. 1.155 g (6.49 mmol, 2.2 eq) of NBS and 335 µl (5.9 mmol, 2 eq) of conc. $H_2SO_4$ are added. It is then heated up to 60° C. for 4.5 hours, checking the reaction with UPLC/MS. After 4.5 hours a mixture was produced, made of 36% of monobromo product, 50% of a mixture of dibromo compounds (with 66% of the desired one) plus other undesired bromine-containing compounds.

Comparative Example C

Preparation of 4,5-dibromo-1H-inden-2-yl-amine (Compound of Formula (I) Wherein R is Hydrogen) in Acetonitrile without Acid In a single neck flask equipped with a reflux, 500 mg (2.95 mmol, 1 eq) of indanamine hydrochloride and 5 ml of $CH_3CN$ are charged. It is stirred at room temperature for 10 minutes. 1.155 g (6.49 mmol, 2.2 eq) of NBS is added. It is heated up to 60° C. for 4.5 h, checking the reaction with UPLC/MS. After 1 hour, checking with UPLC/MS it is found 51% of the starting compound, 10% of monobromo mixture and 40% of a mixture of 3 products with the same mass, which do not contain bromine.

Comparative Example D

Preparation of 4,5-dibromo-1H-inden-2-yl-amine (Compound of Formula (I) Wherein R is Hydrogen) in Ethanol In a single neck flask equipped with a reflux, 500 mg (2.95 mmol, 1 eq) of indanamine hydrochloride and 5 ml of EtOH are charged. It is stirred at room temperature for 10 minutes. 1.155 g (6.49 mmol, 2.2 eq) of NBS and 335 µl (5.9 mmol, 2 eq) of conc. $H_2SO_4$ are added. It is then heated up to 60° C. for 4.5 hours, checking the reaction with UPLC/MS. The reaction mixture after 1 hour contains now 70% of the starting compound, 21% of monobromination mixtures and other impurities and remains substantially unchanged during time.

Comparative Example E

Reproduction of the reaction reported in Adv. Synth. Catal 2001, 343, 461-472

The described procedure can be used to prepare the monobromo indanamine and is specified that for the preparation of the dibromo derivative it is only necessary to double the bromine amount.

Test Carried Out by Doubling the $Br_2$ Only

In a three necks flask equipped with a reflux and a thermometer, 1 g (5.89 mmol, 1 eq) of indanamine hydrochloride and 5 ml of $H_2O$ are charged. It is heated up to 60° C. until dissolution. 760 µl of $Br_2$ (14.72 mmol, 2.5 eq) are added and it is heated up for 1 hour at 60° C. Then 916 µl of HBr (8.25 mmol, 1.4 eq) are added and it is heated up to 60° C. for additional 15 minutes. It is cooled down to room temperature and filtered over buchner, the solid is washed with 10 ml of isopropanol. 1.5 g of product containing 51% of a mixture of monobromo derivatives and 49% of a mixture of dibromo derivatives (with 57% of the desired isomer) are obtained.

Test Carried Out by Doubling the $Br_2$ and also the HBr

In a three necks flask equipped with a reflux and a thermometer, 1 g (5.89 mmol, 1 eq) of indanamine hydrochloride and 5 ml of $H_2O$ are charged. It is heated up to 60° C. until dissolution and 760 µl of $Br_2$ (14.72 mmol, 2.5 eq) are added. It is heated up for 1 hour at 60° C. and then 1.82 ml of HBr (16.5 mmol, 2.8 eq) is added and it is heated up to 60° C. for additional 15 minutes. It is cooled down to room temperature and filtered over buchner, the solid is washed with 10 ml of isopropanol. 1.5 g of product containing 54% of a mixture of monobromo derivatives and 46% of a mixture of dibromo derivatives (with 74% of the desired isomer) are obtained.

The invention claimed is:
1. A process for the preparation of a compound of formula (I)

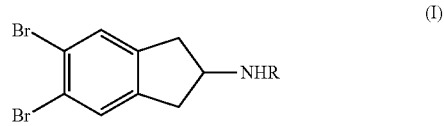

or salts thereof, wherein R is a hydrogen atom or an amine protecting or activating group, comprising reacting 1H-inden-2-yl-amine of formula (II)

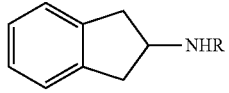
(II)

or a salt thereof, with N-bromosuccinimide (NBS) in water, wherein R is an amine protecting or activating group.

2. The process according to claim 1, wherein the compound of formula (II) is in the form of its hydrobromide or hydrochloride salt.

3. The process according to claim 2, wherein the compound of formula (II) is in the form of its hydrochloride salt.

4. The process according to claim 1, wherein the molar ratio between the compound of formula (II) and NBS is 1:1.8-2.5.

5. The process according to claim 1, wherein the reaction occurs in the presence of an acid.

6. The process according to claim 5, wherein said acid is sulfuric acid.

7. The process according to claim 2, wherein the molar ratio between the compound of formula (II) and NBS is 1:1.8-2.5.

8. The process according to claim 3, wherein the molar ratio between the compound of formula (II) and NBS is 1:1.8-2.5.

9. The process according to claim 2, wherein the reaction occurs in the presence of an acid.

10. The process according to claim 3, wherein the reaction occurs in the presence of an acid.

11. The process according to claim 4, wherein the reaction occurs in the presence of an acid.

12. A process for the preparation of a compound of formula (I)

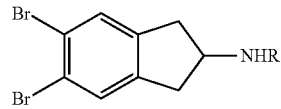
(I)

or salts thereof, wherein R is a hydrogen atom or an amine protecting or activating group, comprising reacting 1H-inden-2-yl-amine of formula (II)

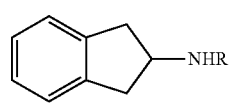
(II)

or a salt thereof, with N-bromosuccinimide (NBS) in water, and desalifying the so-obtained bromide compound and/or converting it in another salt and/or in a derivative, wherein R is an amine protecting or activating group.

13. The process according to claim 12, wherein the compound of formula (II) is in the form of its hydrobromide or hydrochloride salt.

14. The process according to claim 13, wherein the molar ratio between the compound of formula (II) and NBS is 1:1.8-2.5.

15. The process according to claim 12, wherein the molar ratio between the compound of formula (II) and NBS is 1:1.8-2.5.

* * * * *